United States Patent
Elli et al.

(12)

(10) Patent No.: US 6,340,585 B1
(45) Date of Patent: Jan. 22, 2002

(54) SYNTHETIC MEDIUM FOR CULTIVATING LACTOBACILLUS AND BIFIDOBACTERIA

(75) Inventors: Marina Elli, Lausanne; Ralf Zink, Le Mont Pelerin; Barbara Marchesini-Huber, Savigny; Roberto Reniero, Le Mont Pelerin, all of (CH)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 09/532,884

(22) Filed: Mar. 22, 2000

(30) Foreign Application Priority Data

Mar. 23, 1999 (EP) .............................. 99105855

(51) Int. Cl.⁷ ............................ C12N 1/20; C12N 1/00; C12N 1/12
(52) U.S. Cl. ................. 435/252.9; 435/243; 435/252.1; 435/252.4; 435/252.9; 435/253.6; 435/854; 435/855; 435/856
(58) Field of Search .............................. 435/252.9, 243, 435/252.1, 252.4, 253.6, 854–856

(56) References Cited

U.S. PATENT DOCUMENTS 4,544,559 A * 10/1985 Gil et al.

FOREIGN PATENT DOCUMENTS

| CA | 1322732 C | * | 10/1993 |
| EP | 0 460 414 A2 | | 6/1991 |
| EP | 0 656 421 A1 | | 1/1994 |
| JP | 357071390 A | * | 5/1982 |
| JP | 403130071 A | * | 6/1991 |
| SU | 147951 A | * | 5/1989 |

OTHER PUBLICATIONS

Davis et al. Journal of Bacteriology, 126(3): 1136–1140. Incorporation of deoxycytidine into deoxyribonucleic acid deoxycytidylate in *Lactobacillus acidophilus* R–26, Jun. 19, 1976.*

Patent Abstracts of Japan, vol. 007, No. 122 (C–168); JP 58 040096 A, 1991.

Patent Abstracts of Japan, vol. 015, No. 337 (C–0862); JP 03 130071 A, 1983.

* cited by examiner

Primary Examiner—Christopher R. Tate
Assistant Examiner—Michele Flood
(74) Attorney, Agent, or Firm—Winston & Strawn

(57) ABSTRACT

The present invention relates to a novel defined medium suitable to cultivate lactic acid bacteria, such as Lactobaccilus or Bifidobacteria. In particular the present invention pertains to the use of said medium for the isolation of bioactive molecules or functional metabolites.

11 Claims, No Drawings

SYNTHETIC MEDIUM FOR CULTIVATING LACTOBACILLUS AND BIFIDOBACTERIA

FIELD OF THE INVENTION

The present invention relates to a novel synthetic medium suitable to cultivate lactic acid bacteria of the genus Bifidobacteria or Lactobacillus which contains particular nucleotides and deoxynucleotides. In particular, the present invention pertains to the use of said medium for the isolation of bioactive molecules or functional metabolites.

BACKGROUND OF THE INVENTION

Lactobaccili are widely distributed in nature and are largely used for industrial fermentation process, for example, the preparation of dairy products. In recent years the study of their metabolism has been greatly enhanced since particular strains have been found to exert a positive effect on the maintenance of the healthy state of organisms. Their complex nutrient requirements are usually satisfied by natural sources of synthetic growth media, containing matrices of undefined and complex composition, such as yeast extract and peptones of various origins.

Some semi-synthetic and completely chemically defined media have been developed for lactic acid bacteria for different purposes, such as the investigation of the nutritional requirements of bacterial cells, the identification of the role of specific components by detection of the effects after removal thereof from the medium or the isolation of mutants auxotrophic for certain substances. Growth media with a defined chemical composition were also used to determine the requirements of Lactobaccili for nucleotides and to attribute their essential or non-essential role with regard to different DNA precursors.

In the past few decades several studies were performed by means of defined media, on the strain *Lactobacillus johnsonii* ATCC 11506 (formerly known as *Lactobacillus acidophilus* R-26), firstly proposed by Hoff-Jorgensen as an experimental organism for determining the presence of DNA residues in biological samples (Hoff-Jorgenson, "A microbiological assay for deoxyribonucleosides and deoxyribonucleic acid", Biochem J. 50 (1952), 400–403). Ives and Ikeda report in "Life on the salvage path: the deoxynucleoside kinases of *Lactobacillus acidophilus* R26", Progr. Nucl. Acid. Res. (1998), 207–252, that this strain requires the presence of at least one deoxyribonucleoside in the growth medium due to the functional absence of ribonucleotide reductase activity.

Further, it could be shown that in *Lactobaccillus delbrueckii subsp. lactis* ATCC 7830 (formerly known as *L. leichmannii* ATCC 7830), in contrast to strain R-26, the requirement for deoxyribonucleosides could be replaced by Vitamin B12.

The latter strain was subjected to several investigation in order to elucidate the nucleotide requirements of Lactobaccili and the effects of supplementation of the medium with DNA molecules (Jeener & Jeener, Exptl. Cell Res. 3 (1952), 675–680; Okazaki & Okazaki, J. Biochem. 35 (1959), 434–445; Hoff-Jorgensen, Meth. Enzymol. 3 (1957), 781–785; Mc Nutt Meth. Enzymol. 2 (1955), 464–468; Lovtrup & Shugar J. Bacteriol. 82 (1961), 623–631.

Thymidine was often indicated as a key factor for the growth of *Lactobacillus acidophilus* and *L. leichmannii*. Further, in later studies the removal of uracil was demonstrated to deeply affect RNA synthesis and cell division in lactic acid bacteria.

In J. Bacteriol. 73 (1957), 670–675 Siedler et al., reported an optimization of Hoff-Jorgensen's medium by studying the ability of uracil, vitamin, vitamin B6 and acid-hydrolized casein to reproduce the positive effect of yeast extract on *L. acidophilus* development in a semi-defined medium.

Recently, Imbert & Blondeau disclosed in Curr. Microbiol. 37 (1998), 64–66, a chemically defined medium for examining the ability of some Lactobacillus species to grow after iron chelation. Furthermore, the interaction between manganese and iron was examined. The supplement of chelated iron did not affect bacterial growth in the presence of manganese, while a slightly positive effect was observed following to the addition thereof to the same medium deprived of manganese especially for *L. acidophilus* ATCC 4346T after aerobic incubation.

It is known that most pathogenic bacteria require iron for their growth. In contrast, lactic acid bacteria have been generally recognized as exceptions among the living organisms in that they do not show such an indispensable iron requirement. This is considered to represent an ecological advantage against pathogens in natural environments.

Few publications exist reporting the average content of metal in lactic acid bacteria. In general, a strong variability among the Lactobacillus species has been found exemplified by a comparison between the iron content of *Lactobacillus plantarum* and *Escherichia coli* cells in which a lower level in the former species was confirmed (Archibald et al., FEMS Microbiol. Lett. 19 (1983), 29–32).

Recently, particular strains of the genus Lactobacillus and Bifidobacteria have attracted great attention since properties beneficial to the host organism have been attributed to them. So far it is only known that these strains exhibit the properties reported, yet the reason for these properties was not elucidated.

In this respect EP 0 577 903 discloses the use of lactic acid bacteria, especially a Lactobacillus strain which upon ingestion reveals beneficial effects to organisms infected by *Helicobacter pylori*. Accordingly, the Lactobacillus is obviously capable of producing metabolites that are capable preventing further growth and/or adhesion of Helicobacter to gastric and/or intestinal mucosal structures. From the point of view of identifying these metabolites, it would be desirable to have a medium from which compounds produced by the lactic acid bacteria may be isolated.

In order to isolate said compounds, the bacterial cells shall be cultivated to a reasonable extent in the medium. Yet media providing a sufficient growth of lactic acid bacteria are normally not defined and comprise complex matrices, such as yeast extract and peptones, from which a desired, still unknown compound cannot be isolated.

On the other hand, known defined media are normally specific for a given bacterial strain, and moreover do not provide for sufficient growth of the microorganism.

SUMMARY OF THE INVENTION

Consequently, a problem of the present invention is how to provide a novel defined medium, which allows for a sufficient growth of plurality of different bacterial strains?

This problem was solved by providing a synthetic medium for cultivating lactic acid bacteria belonging to the genus Lactobacillus or Bifidobacteria comprising a carbon source, buffer, a nitrogen source, trace elements, antioxidants and vitamins characterized in that it contains two free bases, one ribonucleoside and two 2'-deoxynucleosides, each in an amount sufficient to promote growth of the microorganisms.

During the extensive studies leading to the present invention, a chemically defined growth medium for *Lactobacillus johnsonii* was developed, which was surprisingly found to be suitable for the cultivation of other Lactobacilli and/or Bifodobacteria as well. In the experiments, particular attention was paid to the nucleotide composition of the medium and several sources of DNA precursors were examined for the ability to support Lactobacillus/Bifidobacteria growth.

DETAILED DESCRIPTION OF THE INVENTION

To this end a defined medium for *L. johnsonii* was supplemented with free bases (adenine, cytosine, guanine, thymine, uracil and inosine), ribonucleosides (adenosine, cytindine, guanosine, uridine) and deoxyribonucleosides (2'-deoxyadenosine, 2'-deoxycytidine, 2'-deoxyguanosine, 2'-deoxyuridine and thymidine). The different Lactobacilli investigated had the ability to grow in the defined medium in the simultaneous presence of all the five free bases, all four ribonucleosides and all the five deoxyribonucleosides. Whereas, the minimal requirement for substantial growth was found to be a combination of at least two free bases, one nucleosides and two deoxyribonucleosides.

It could be shown that both adenine and guanine could be replaced by inosine as precursor and the requirement for thymine and cytosine could be satisfied by supplementation of the medium with uracil. The presence of inosine and uracil was found to be beneficial for the growth of some Lactobacillus species, confirming their inability to substantially synthesize purines and pyrimidines de novo.

Supplementation of the defined medium with the above-mentioned minimally required compounds increased the final cell counts. However, optimal results were obtained with a combination of the following nucleotide derivatives: guanine, thymine, cytidine, deoxyadenosine and deoxyuridine.

This particular recipe was also used to investigate the iron requirements of Lactobacilli by means of several defined recipes differing in their nucleotide composition. Little differences in the optical density values were observed after 18 hours of incubation at 37° C., after removal of the iron compound when the minimal number of the required nucleotide precursors were supplied.

Stronger effects of iron removal were detected if inosine and uracil were supplied as the only nucleotide sources. Further investigations demonstrated that the negative effect of iron omission was emphasized after uracil replacement with cytosine. Therefore, a putative role of iron in the metabolism of pyrimidines or purines of Lactobaccili/Bifidobacterium was proposed. It is concluded that Lactobillus spp., particularly *L. johnsonii*, require iron only under particular environmental conditions. Yet, when supplementing a synthetic medium with at least two free bases, one ribonucleoside and two deoxyribonucleosides as nucleotide precursors, substantial growth of different Lactobacilli and Bifidobacteria could be shown, without the need to add iron to the medium. This feature proves to be rather advantageous since contamination of cultures with bacteria requiring iron for their growth may be limited when the media does not contain iron.

As a carbon source for the medium, any source well known in the art, for example fructose, lactose, saccharose or mixtures thereof, may be selected. In order to provide a pH-value adapted to the specificity of the particular strains, the medium may contain any sort of buffer used in the art, such as $KH_2PO_4/K_2HPO_4$, diammoniumhydrogencitrate, $NaHCO_3/Na_2CO_3$ or mixtures thereof.

The medium further contains a nitrogen source which may preferably be selected from any of the natural amino acids or diammoniumhydrogencitrate or mixtures thereof.

The medium further contains antioxidants, so as to provide a suitable environment for growth. Antioxidants are well known in the art, such as ascorbic acid, cystein, thiol compounds or mixtures thereof. For the purpose of reducing the number of different compounds included in the synthetic medium cysteine is preferred as such an antioxidant.

Further, the medium contains trace elements required for the growth of the microorganisms. Said trace elements are, for example, Cu-, Zn-, Mn-, Mg-, Co-compounds, or mixtures thereof. For the purpose of reducing the amount of compounds in the medium the counter ion is preferably selected from another organic compound to be added to the medium, such as citrate, or may be a negatively charged ion, such as Cl etc.

The medium additionally contains different vitamins, such as nicotinic acid, panthotenate, cobalamine, p-aminobenzoic acid, pyridoxal-HCl, riboflavin, biotin, folic acid or mixtures thereof.

It will be appreciated that the skilled person will, based on his own knowledge, use compounds not explicitly listed above, yet providing for the same purpose.

It was found that a preferred amount for the nucleotide precursors to be included in the medium ranges from about 0.5 g to about 0.3 g/l, preferably about 0.1 g/l.

Due to its defined composition, the present medium may be used for the identification and/or isolation of bioactive molecules and/or functional metabolites, respectively, produced by Lactobacilli and/or Bifidobacteria. In this respect the bacteria are grown in the medium. Since this medium provides for a suitable growth environment, high cell count may be achieved, with the result that also a substantial amount of bioactive molecules/functional metabolites may be produced.

Isolation of metabolites secreted by the microorganism may be accomplished by centrifugation of the defined cultivation medium at high speed, so as to deplete it of any bacterial cells. The supernatant may then be collected and further analyzed for biological compounds according to techniques well known in the art.

In the following section the invention is described by means of examples. The examples are not meant to be construed as limitations to the invention.

EXAMPLE

Bacterial strains:

For the experiments the following different strains were used:

TABLE 1

Origin of investigated bacterial strains

| Strain | Source |
| --- | --- |
| L. johnsonii ATCC 33200[T] | American Type Culture Collection |
| L. johnsonii ATCC 11506 | American Type Culture Collection |
| L. johnsonii Lal (NCC 533) | Nestec Culture Collection |
| L. johnsonii ATCC 332 | Deutsche Samm lung fi. ir Mikroorganismen |
| L. johnsonii DSM 20553 | Deutsche Sammiung fir Mikroorganismen |
| L. gasseri DSM 20243[T] | Deutsche Sammlung fir Mikroorganismen |
| L. gallinarum DSM 33199[T] | Deutsche Sammlung fir Mikroorganismen |
| L. casei ATCC 393[T] | American Type Culture Collection |
| L. paracasei NCDO 151[T] | National Collection of Dairy Organism (now NCFB) |
| L. plantarum NCDO 1193 | National Collection of Dairy Organism (now NCFB) |
| L. helveticus ATCC 10386 | American Type Culture Collection |
| L. delbrueckii subsp. delbrueckii DSM 20074[T] | Deutsche Sammlung fir Mikroorganismen |
| L. delbrueckii subsp. lactis ATCC 7830 | American Type Culture Collection |

The microorganisms were propagated in MRS (Difco) broth or agar at 37° C. Two sub-culturing steps of 18 hours each were performed from a frozen culture prior to performing the tests.

Media:

The composition of a defined medium (DM1) is indicated in Table 2, below:

TABLE 2

Medium composition of the defined medium

| Constituent | Final concentration (g/l) |
| --- | --- |
| Glucose | 10 |
| Potassium hydrogen phosphate | 3.1 |
| di-ammonium hydrogen citrate | 2 |
| Potassium dihydrogen phosphate | 1.5 |
| Sodium chloride | 0.02 |
| Ascorbic acid | 0.5 |
| Potassium acetate | 10 |
| Tween 80 | 1 |
| Heptahydrated magnesium sulphate | 0.5 |
| Hydrated manganese sulphate | 0.02 |
| Cobalt sulphate | 0.5 |
| Calcium lactate | 1 |
| DL-alanine | 0.2 |
| DL-aminobutyric acid | 0.1 |
| Glycine | 0.2 |
| L-histidine HCl | 0.2 |
| L-lysine HCl | 0.2 |
| L-phenylalanine | 0.1 |
| L-proline | 0.2 |
| L-serine | 0.1 |
| L-threonine | 0.1 |
| L-cysteine | 0.1 |
| L-arginine | 0.2 |
| L-aspartic acid | 0.3 |
| L-asparagine | 0.1 |
| L-glutamic acid | 0.3 |
| L-isoleucine | 0.1 |
| L-leucine | 0.2 |
| L-methionine | 0.1 |
| L-tyrosine | 0.1 |
| L-tryptophan | 0.1 |
| L-valine | 0.1 |
| Nicotinic acid | 10 mg |
| Calcium pantothenate | 10 mg |
| Cyanocobalamin | 0.02 mg |
| Para-aminobenzoic acid | 0.2 mg |
| Myo-inositol | 10 mg |
| Pyridoxal HCl | 10 mg |
| Riboflavin | 10 mg |
| Biotin | 1 mg |
| Folic acid | 0.2 mg |
| Guanine | 0.1 |
| Thymine | 0.1 |
| Cytidine | 0.1 |
| 2'-deoxyadenosine | 0.1 |
| 2'-deoxyuridine | 0.1 |

The above recipe lacks iron. Iron was supplemented as ferrous sulphate ($FeSO_4 7H_2O$) (0.02 g/l final concentration) dissolved in sterile distilled water, freshly prepared each time and immediately added to the medium. It was filter-sterilized or autoclaved (121° C.). Each listed component was supplied by Sigma Chemicals. The nucleotides indicated in the recipe represent the optimal combination capable to support L. johnsonii growth at a high level.

Other nucleotide derivatives were tested:

| | |
| --- | --- |
| Free bases | adenine, guanine, cytosine, uracil, thymine; |
| ribonucleosides | adenosine, cytidine, guanosine, uridine; and |
| deoxyribonucleosides | 2'-deoxyadenosine, 2'-deoxyguanosine, 2'-deoxycytidine, 2'-deoxyuridine, thymidine, | that were supplied as neutral or alkaline solutions with the same final concentration indicated in Table 2.

Viable cells and optical density measurement:

The number of viable cells was determined by decimal counts after anaerobic incubation for 48 hours on agar MRS (Difco) plates as 37° C. The optical density was measured at 560 nm using a Dye UNICAM PU8660 spectrophotometer. The reported growth results raise from the average of three trials.

Inoculum preparation:

The tested defined media were 1% inoculated from an MRS culture, washed twice and finally resuspended with the same amount of sterile distilled water in order to avoid nutrient transfer via the medium.

Incubation parameters:

The tubes were incubated at 37° C. for 18 hours. The defined medium, as above, was optimized in composition for L. johnsonii for the ability to achieve high growth level. After 18 hours incubation at 37° C., 1.8 logs in average were gained for all the strains listed above.

As may be derived from Table 2, the medium contains a combination of different DNA derivatives (two free bases, one ribonucleoside and two 2'-deoxyribonucleosides). Another mix of nucleotides was tested which presented inosine as purine precursor and uracil as the only essential pyrimidine base. The modified medium supported the growth of the strains in a range of 1.5–2 logs increasing after 18 hours incubation.

Omission of all the DNA and RNA precursors resulted in an almost complete growth inhibition of almost all of the tested species except for L. casei subsp. casei, L. casei susbp. paracasei and L. plantarum which were not affected by this depletion, confirming that they can synthesize purines and pyrimidines de novo, allowing the build up of the nucleotide ring directly on the activated ribose molecule.

The other strains tested required at least inosine and uracil to synthesize the nucleotides pool essential for RNA and DNA synthesis. The commission of iron did not affect the ability of the tested strain to grow in this depleted medium as seen in Table 3 below:

TABLE 3

Effect of iron removal from the defined medium DM1

| Strain | | Final growth yield(a) DM1 | DM1 (b) |
|---|---|---|---|
| L. johnsonii | ATCC 33200$^T$ | 1.65 | 1.75 |
| L. johnsonii | ATCC 11506 | 0.67 | 0.65 |
| L. johnsonii | La1 (NCC 533) | 1.71 | 1.76 |
| L. johnsonii | DSM 20553 | 1.10 | 1.20 |
| L. gasseri | DSM 20243$^T$ | 1.50 | 1.41 |
| L. gallinarum | DSM 33199$^T$ | 1.97 | 2.00 |
| L. casei | ATCC 393$^T$ | 1.95 | 1.93 |
| L. paracasei | NDCO 151$^T$ | 1.12 | 1.30 |
| L. delbrueckii subsp. delbrueckii | DSM 20074 | 1.40 | 1.52 |
| L. plantarum | NCDO 151$^T$ | 1.30 | 1.35 |
| L. delbrueckii subs.. lactis | ATCC 7830 | 1.90 | 1.94 |

(a)Results expressed as O.D. at 560 nm
(b) DM1 recipe deprived of ferrous sulphate Different nucleotide sources were added to the medium to replace the DM1 nucleotide composition. Five free bases (adenine, cytosine, guanine, thymine and uracil), four ribonucleosides (adenosine, cytidine, guanosine and uridine) or five 2'-deoxyribonucleosides (deoxyadenosine, deoxyguanosine, deoxycytidine, deoxycytidine, deoxyuridine, thymidine) were supplied and the corresponding media were termed DM3, DM4 and DM5, respectively (Table 4).

The performance of the strains tested towards different DNA derivatives was determined by measuring the O.D. values at 560 nm. Table 5 shows the final growth yield achieved both when the strains were grown in the modified media and when iron, in form of ferrous sulphate, was omitted. The results showed no strong effects of this removal according to the absence of a clear iron requirement of Lactobacilli.

TABLE 5

Effect of ferrous sulphate depletion from the medium DM2 on Lactobacilli growth

| Strain | Final growth yield (a) DM2 | Final growth yield (a) DM2(b) |
|---|---|---|
| L. johnsonii ATCC 33200 T | 0.82 | 0.46 |
| L. johnsonii Lal(NCCS33) | 1.13 | 0.67 |
| L. johnsonii ATCC 11506 | 0.57 | 0.15 |
| L. johnsonii ATCC 332 | 1.10 | 0.65 |
| L. johnsonii DSM 20553 | 1.20 | 0.36 |
| L. gasseri DSM 20243 T | 0.82 | 0.57 |
| L. gallinarum ATCC 33199 T | 0.82 | 0.50 |
| L. casei ATCC 393 T | 1.24 | 1.23 |
| L. paracasei NCDO 151 T | 1.16 | 1.02 |
| L. delbrueckii DSM 20074 T | 0.85 | 0.52 |
| L. plantarum NCDO 1193 | 1.38 | 1.38 |
| L. lactis ATCC 7830 | 1.20 | 1.14 |
| L. helveticus ATCC 892 | 1.13 | 0.84 |

(a) results expressed as O.D. at 560 nm
(b)depletion of ferrous sulphate

As expected L. johnsonii ATCC 11506 developed rather poorly in this medium but the effect of iron removal was slightly observable.

The iron deprivation was also applied to the DM2 medium characterized by the presence of inosine and uracil ad nucleotide sources (Table 4 and 6). In this case a stronger effect was observed especially for L. johnsonii, L. gasseri, L. gallinarum and L. helveticus which showed a significant decrease in the optical density values after incubation in the DM2 medium deprived of ferrous sulphate.

TABLE 4

Effect of free bases, ribonucleosides and deoxyribonucleosides on Lactobacilli growth and performance after iron depletion

| | Final growth yield (a) | | | | | |
|---|---|---|---|---|---|---|
| Strain | DM3 | DM3 (b) | DM4 | DM4 (b) | DM5 | DM5 (b) |
| L. johnsonii ATCC 33200 T | 1.00 | 0.97 | 1.13 | 1.10 | 0.92 | 0.48 |
| L. johnsonii La1 (NCC 533) | 0.78 | 0.75 | 1.16 | 0.86 | 1.14 | 0.95 |
| L. johnsonii ATCC 11506 | 0.68 | 0.69 | 0.67 | 0.56 | 0.93 | 0.94 |
| L. johnsonii DSM 20553 | 0.78 | 0.74 | 1.04 | 0.85 | 1.07 | 1.04 |
| L. gasseri DSM 20243 T | 0.92 | 0.95 | 0.92 | 0.87 | 0.88 | 0.86 |
| L. gallinarum ATCC 33199 T | 0.41 | 0.37 | 0.78 | 0.71 | 1.05 | 0.93 |
| L. casei ATCC 393 T | 0.91 | 0.87 | 1.24 | 1.23 | 1.21 | 1.22 |
| L. paracasei NCDO 151 T | 1.00 | 1.02 | 0.98 | 0.94 | 1.03 | 1.08 |
| L. delbrueckii DSM 20074 T | 0.15 | 0.15 | 0.34 | 0.29 | 0.26 | 0.25 |
| L. lactis ATCC 7830 | 0.84 | 1.03 | 1.12 | 1.12 | 0.96 | 1.11 |
| L. helveticus ATCC 892 | 0.04 | 0.04 | 0.11 | 0.07 | 0.05 | 0.06 |

(a) results expressed as O.D. at 560 nm
(b) omission of ferrous sulphate

TABLE 6

Effect of adenine, guanine, inosine, uracil, cytosine and orotic acid on *L. johnsonii* growth in the defined medium DM1 with and without ferrous sulphate addition

| | *L. johnsonii* strains | | | | |
|---|---|---|---|---|---|
| Medium | ATCC 33200 T | La1(NCC 533) | ATCC 11506 | ATCC 332 | DSM 20553 |
| (A) + FeSO$_4$ | 0.72 | 1.14 | 0.57 | 0.97 | 1.11 |
| (A) − FeSO$_4$ | 0.48 | 0.19 | 0.21 | 0.41 | 0.41 |
| (B) + FeSO$_4$ | 0.86 | 1.05 | 0.58 | 0.23 | 1.15 |
| (B) − FeSO$_4$ | 0.12 | 0.13 | 0.16 | 0.10 | 0.16 |
| (C) + FeSO$_4$ | 0.43 | 1.07 | 0.52 | 0.77 | 1.06 |
| (C) − FeSO$_4$ | 0.51 | 0.17 | 0.21 | 0.52 | 0.39 |
| (D) + FeSO$_4$ | 0.25 | 0.23 | 0.31 | 0.24 | 0.26 |
| (D) − FeSO$_4$ | 0.16 | 0.12 | 0.18 | 0.15 | 0.21 |
| (E) + FeSO$_4$ | 0.36 | 0.34 | 0.31 | 0.47 | 0.35 |
| (E) − FeSO$_4$ | 0.40 | 0.25 | 0.30 | 0.50 | 0.48 |
| (F) + FeSO$_4$ | 0.44 | 0.39 | 0.49 | 0.62 | 0.89 |
| (F) − FeSO$_4$ | 0.43 | 0.30 | 0.41 | 0.25 | 0.38 |
| (G) + FeSO$_4$ | 0.33 | 0.49 | 0.49 | 0.67 | 0.89 |
| (G) − FeSO$_4$ | 0.40 | 0.29 | 0.33 | 0.32 | 0.47 |
| (H) + FeSO$_4$ | 0.31 | 0.28 | 0.43 | 0.25 | 1.06 |
| (H) − FeSO$_4$ | 0.21 | 0.22 | 0.32 | 0.24 | 0.23 |

(A) DM1 + inosine, uracil = DM2
(B) DM1 + inosine, cytosine;
(C) DM1 + inosine, uracil, cytosine;
(D) DM1 + cytosine;
(E) DM1 + inosine, orotic acid;
(F) DM1 + adenine, guanine, orotic acid;
(G) DM1 + adenine, guanine, uracil;
(H) DM1 + adenine, guanine, cytosine.

What is claimed is:

1. A synthetic medium for cultivating a plurality of lactic acid bacteria strains belonging to the genus Lactobacillus and/or Bifidobacteria comprising a carbon source; a buffer; a nitrogen source; one or more of trace elements, antioxidants and vitamins; at least two free bases selected from the group consisting of adenine, cytosine, guanine, thymine, uracil and inosine; one ribonucleoside selected from the group consisting of adenosine, cytidine, guanosine and uridine; and two different 2'-deoxynucleosides selected from the group consisting of 2'-deoxyadenosine, 2'-deoxycytidine, 2'-dioxyguanosine, 2'-deoxyuridine and thymidine, wherein each is present in an amount which in combination is sufficient to promote growth of the bacteria.

2. A synthetic medium for cultivating a plurality of lactic acid bacteria strains belonging to the genus Lactobacillus and/or Bifidobacteria comprising a carbon source; a buffer; a nitrogen source; trace elements; antioxidants; vitamins; at least two free bases selected from the group consisting of adenine, cytosine, guanine, thymine, uracil and inosine; one ribonuceloside selected from the group consisting of adenosine, cytidine, guanosine and uridine; and two different 2'-deoxynucleosides selected from the group consisting of 2'-deoxyadenosine, 2'-deoxycytidine, 2'-dioxyguanosine, 2'-deoxyuridine and thymidine, wherein each is present in an amount which in combination is sufficient to promote growth of the bacteria.

3. The medium of claim 2, wherein the carbon source comprises glucose, fructose, lactose, saccharose, or a mixture thereof.

4. The medium of claim 2, wherein the buffer comprises $KH_2PO_4/K_2HPO_4$, diammoniumhydrogencitrate, $NaHCO_3/Na_2CO_3$ or a mixture thereof.

5. The medium of claim 2, wherein the nitrogen source comprises one or more amino acids, diammoniumhydrogencitrate or any mixture thereof.

6. The medium of claim 2, wherein the antioxidant comprises ascorbic acid, cysteine, thiol compounds or any mixture thereof.

7. The medium of claim 2, wherein the trace elements comprise Cu-, Zn-, Mn-, Mg-, Co-compounds or any mixture thereof.

8. The medium of claim 2, wherein the vitamins comprise nicontinic acid, pantothenate, cobalamine, para-amino benzoic acid pyridoxal-hydrochloride, riboflavin, biotin, folic acid or any mixture thereof.

9. The medium of claim 2, wherein the nucleotides and deoxynucleotides comprise about 0.1 g/l to about 0.5 g/l.

10. A method of growing lactic acid bacteria belonging to the genus Lactobacillus and/or Bifidobacteria which comprises cultivating the bacteria on the synthetic medium of claim 1 or 2.

11. A method of producing a bioactive molecule, which comprises cultivating a bacteria belonging to the genus Lactobacillus and/or Bifidobacteria in the synthetic medium of claim 1 or 2 to produce a bioactive molecule in the synthetic medium, separating the bacteria from the medium and isolating the bioactive molecule from the medium.

* * * * *